(12) United States Patent
Barboutis et al.

(10) Patent No.: US 8,435,191 B2
(45) Date of Patent: May 7, 2013

(54) SUPPORT STRUCTURE FOR A SENSOR STRIP AND SENSOR STRIP FOR MOUNTING ON SAID SUPPORT STRUCTURE

(75) Inventors: Grigorios Barboutis, Berlin (DE); Dirk David Goldbeck, München (DE); Tobias Happel, Berlin (DE); Andre Matthias Kwiatek, Berlin (DE); Stefan Nerreter, Heidesee OT Blossin (DE)

(73) Assignee: Siemens Aktiengesellschaft, Munich (DE)

( * ) Notice: Subject to any disclaimer, the term of this patent is extended or adjusted under 35 U.S.C. 154(b) by 371 days.

(21) Appl. No.: 12/669,321

(22) PCT Filed: Jul. 15, 2008

(86) PCT No.: PCT/EP2008/059253
§ 371 (c)(1),
(2), (4) Date: May 28, 2010

(87) PCT Pub. No.: WO2009/010518
PCT Pub. Date: Jan. 22, 2009

(65) Prior Publication Data
US 2010/0240981 A1    Sep. 23, 2010

(30) Foreign Application Priority Data

Jul. 18, 2007  (DE) .......................... 10 2007 034 264
Sep. 26, 2007  (DE) .......................... 10 2007 046 826

(51) Int. Cl.
*A61B 5/00*   (2006.01)
*A61B 5/103*  (2006.01)
*A61B 5/11*   (2006.01)

(52) U.S. Cl.
USPC .............................. 600/587; 600/595; 398/16

(58) Field of Classification Search .................. 600/587, 600/595; 73/379.01; 398/16
See application file for complete search history.

(56) References Cited

U.S. PATENT DOCUMENTS 3,608,541 A    9/1971  Hall
5,226,417 A *  7/1993  Swedlow et al. ............. 600/336
(Continued)

FOREIGN PATENT DOCUMENTS

DE    42 05 790     9/1993
GB    2 337 157     1/2003
(Continued)

OTHER PUBLICATIONS

German Office Action issued Apr. 21, 2008 in corresponding German Application No. 10 2007 046 826.3-35.

(Continued)

*Primary Examiner* — Sean Dougherty
(74) *Attorney, Agent, or Firm* — Staas & Halsey LLP

(57) ABSTRACT

The embodiments relate to a sensor strip (13) and to a flexible support strip (12) for receiving the sensor strip and for fixing the strip to a surface e.g. to the back of a test person. According to the embodiments, the sensor strip (13) has a reference point (18), (for example a snap fastener connection), with which it can be fixed to a reference surface (16) of the support strip. This allows the position of the sensor strip (13) to be unambiguously defined on the support strip (12). The further extension of the sensor strip (13) lies in a pocket (23) so that it can slide, allowing the relative movement between the support strip and the sensor strip if the support strip is lengthened (represented by a dot-dash line). The entire sensor unit is thus advantageously more comfortable to wear, as the elastic support strip (12), for example, can freely follow the back movements of the test person.

6 Claims, 1 Drawing Sheet

U.S. PATENT DOCUMENTS

| | | | |
|---|---|---|---|
| 5,316,017 A | 5/1994 | Edwards et al. | |
| 5,690,610 A * | 11/1997 | Ito et al. | 602/53 |
| 6,032,530 A | 3/2000 | Hock | |
| 6,360,615 B1 * | 3/2002 | Smela | 73/862.474 |
| 6,487,906 B1 * | 12/2002 | Hock | 73/379.01 |
| 7,033,281 B2 | 4/2006 | Carnahan et al. | |
| 7,869,849 B2 * | 1/2011 | Ollerdessen et al. | 600/323 |
| 7,869,850 B2 * | 1/2011 | Hoarau et al. | 600/344 |
| 7,899,510 B2 * | 3/2011 | Hoarau | 600/344 |
| 8,291,779 B2 * | 10/2012 | Helmer et al. | 73/865.4 |
| 2007/0293781 A1 * | 12/2007 | Sims et al. | 600/534 |
| 2009/0143704 A1 * | 6/2009 | Bonneau et al. | 600/595 |

FOREIGN PATENT DOCUMENTS

| | | |
|---|---|---|
| WO | WO 97/43953 | 11/1994 |
| WO | WO 01/58538 | 8/2001 |

OTHER PUBLICATIONS

Cure-Tape® characteristics, http://www.tapeconcept.com/characterisitics.html.

www.medicaltaping.de/Die%20Geschichte-kinesio-medi-taping-concept, Die Geschichte Medical Taping, Nov. 25, 2010, pp. 1-4.

* cited by examiner

SUPPORT STRUCTURE FOR A SENSOR STRIP AND SENSOR STRIP FOR MOUNTING ON SAID SUPPORT STRUCTURE

CROSS REFERENCE TO RELATED APPLICATIONS

This application is the U.S. national stage of International Application No. PCT/EP2008/059253, filed Jul. 15, 2008 and claims the benefit thereof. The International Application claims the benefits of German Application No. 10 2007 034 264.2, filed on Jul. 18, 2007, and Germany Application No. 10 2007 046 826.3, filed on Sep. 26, 2007, all applications are incorporated by reference herein in their entirety.

BACKGROUND

1. Field

The embodiments relate to a flexurally limp carrier structure for a sensor tape (strip) for near-contour fastening on a surface, in particular that of a human or animal body.

2. Description of the Related Art

A flexurally limp carrier structure of the type initially mentioned is known, for example, from U.S. Pat. No. 7,033,281 B2. The carrier structure consists of a sleeve which carries a sensor tape for determining the bending angle of the elbow of a human arm. For measurement purposes, the sleeve is pushed onto the arm, and it surrounds the arm over the entire circumference and is positioned in such a way that the elbow is located in the sleeve. When the bending angle of the elbow joint is changed, this can be detected as a result of the bending of the sensor tape. It is assumed in this case that the sleeve causes a certain restriction in freedom of movement of the arm.

SUMMARY

An aspect of the embodiments is to specify a carrier structure for a sensor tape (strip) which, after near-contour fastening on the surface, influences as little as possible a movement of the body which forms the surface.

This aspect is achieved according to the embodiments, by the carrier structure initially specified, in that the carrier structure has for the sensor tape a channel in which the sensor tape can be mounted so as to be longitudinally displaceable. As a result of the longitudinally displaceable mounting, the carrier structure can advantageously be stretched or compressed independently of the sensor tape when the surface, for example the back of a human body, executes movements. In this case, the sensor tape slides with low resistance in the channel, the channel in this case advantageously giving rise to a near-contour guidance of the sensor tape, so that the bending of the surface can advantageously be measured with high accuracy. For this purpose, according to the embodiments, there is provision for the carrier structure to be elastic in the direction of run of the channel. The advantage can be explained in a simple way, particularly when the carrier structure is used, as already mentioned, on a back. When the spinal column experiences different curvatures (for example, flexion and extension, that is to say bends forward and back), the skin of the back is stretched or contracted. In order to ensure advantageously high wearing comfort, along with as little disturbance of the natural movement sequence as possible, the elastic carrier structure can copy this movement in that it is fixed on the back. For this purpose, for example, a skin-compatible adhesive which firmly connects the carrier structure lengthwise to the back is suitable.

Furthermore, so that as accurate a measurement of the bending of the back as possible can be carried out, there is provision, according to the embodiments, for the carrier structure to have an essentially punctiform fixing device, by which the sensor tape can be held non-displaceably on the sensor tape at a reference point. What is meant by an essentially punctiform fixing device is that the sensor tape is held only at one location, preferably one end, so that the remaining part of the sensor tape is displaceable in the channel. This becomes necessary since the sensor tape is designed to be substantially more rigid in terms of elongation than the elastic carrier structure. On the other hand, a reliable positioning of the sensor structure on the back or on another surface must be ensured, so that the sensor tape cannot slip to and fro in an undefined way in the channel so as to give rise to measurement errors.

According to one refinement of the embodiments, there is provision for the channel to be, in the non-deformed state of the carrier structure, longer than that part of the sensor tape which is to be guided in it. What is advantageously achieved thereby is that a guidance of the sensor tape in the channel is possible both during a shortening and during a lengthening of the carrier structure. When a back sensor is used, therefore, both flexion and extension can be executed if the carrier structure is placed on the back when the latter is straightened.

A further refinement of the embodiments is obtained when the carrier structure has a carrier tape which can be fastened with one side on the surface and the other side of which forms a wall part of the channel. A carrier structure is thereby obtained which is advantageously largely adapted to the geometry of the tape. As a result, this carrier structure can advantageously be attached comparatively conveniently to the surface, in particular skin, of a test person. Contrary to the sleeve according to the prior art, the carrier structure does not constrict the object to be measured, with the result that freedom of movement is largely preserved. Also, because of the minimal use of material, the effort required for the elastic deformation of the carrier structure is advantageously reduced, and therefore the test person feels that it is less troublesome to wear the carrier tape.

In another refinement of the embodiments, the carrier tape at least essentially preserves its width independently of its elongation. This may be achieved, for example, by fabric tapes, the width of which does not change during lengthening or shortening. Tapes of this type are sold, for example, under the trade name of CureTape® manufactured by TapeConcept, Ltd. Of Larnaca, Cypress. The following advantages are pre-eminently achieved by a tape of constant width as the carrier structure. On the one hand, in the event of stretching, such as is observed, for example, on the back, the skin (in general, the surface) is not forced into unnatural deformations by the tape contracting in the transverse direction, since, for example in the case of a flexion of the back, the skin likewise performs only elastic deformations in bending directions. A further advantage is that the channel formed on the carrier structure maintains essentially the same width in the event of a bending of the carrier structure, so that a low-force sliding of the sensor tape in the channel is still ensured independently of the bending line of the carrier tape (at least within a defined operating range).

Furthermore, it is advantageous if the channel is formed by an elastic textile strip which is firmly connected, at least along its side margins, to the remaining carrier structure so as to form a pocket. The elastic textile strip advantageously fits snuggly onto the base on which it is fastened. This base is formed by the larger part of the carrier structure. If, then, a sensor tape is to be fastened to the carrier structure, this sensor tape can advantageously be pushed in a simple way into the pocket formed. In this case, the textile strip yields so that the sensor tape, even having a thickening, for example an evaluation unit located at the end, can be pushed into the channel formed. In this case, by virtue of the restoring forces of the elastic textile strip, a certain pressure force is exerted on the sensor tape, so that the latter bears reliably against the carrier structure. At the same time, however, displaceability in the longitudinal direction of the pocket-shaped channel is preserved.

The combination of a carrier structure in the form of a carrier tape with the elastic textile strip is particularly advantageous. The carrier tape in this case merely has to be designed with a width such that a reliable connection of the carrier structure to the textile strip can be ensured on both sides of the channel. In this case, it is particularly advantageous if the textile strip has a lower rigidity under extension than the remaining carrier structure, in particular the carrier tape. A division of tasks is thereby advantageously achieved, such as is already indicated above in connection with the use of the carrier structure and the flexible textile strip. The textile strip reliably presses the sensor tape against the carrier structure and in this case at the same time allows a largely force-free guidance of the sensor tape in the channel. The carrier structure (in particular, tape-shaped) makes it possible to have a reliable fastening on the surface (back) and in this case at the same time allows a change in length of this surface.

Furthermore, it is advantageous if the channel is formed by guard bridges which are spaced apart from one another and which are fixed on the carrier structure in a longitudinal orientation with respect to the channel, and span the place of installation of the sensor tape. Guard bridges of this type thus form bridge-like guide elements for the sensor tape and thereby form the channel provided for guidance. Moreover, the spaced-apart fixing on the carrier tape makes it possible to have the already addressed change in length of the carrier tape (or of the carrier structure), since, in the event of an elastic deformation of the carrier tape, the spacing between the individual guard bridges is variable.

The guard bridges have the essential advantage that the sensor tape can be protected against damage. In use as a back sensor, it is possible, for example, that the test person leans against a table edge which locally cuts into the sensor tape transversely with respect to the longitudinal extent of the latter. This may lead to highly falsified measurement results or damage (for example, a break) of the sensor tape. The guard bridges are designed to be sufficiently stable to absorb such actions of force upon the sensor tape.

Of course, the use of guard bridges may also be combined with an elastic textile strip for forming the channel. In this case, a division of tasks is advantageously achieved, the guidance of the sensor tape being assumed preeminently by the pocket-shaped channel of the textile strip. The guard bridges then span this pocket at a specific distance from the sensor tape, so that contact does not occur under normal operating conditions. The advantage of this is that a certain elastic deformation of the guard bridges may be tolerated when these absorb forces which are imparted to the carrier structure. As a result, the guard bridges may be designed so as to be less robust, thus advantageously improving the wearing comfort of the carrier structure.

In addition, it is advantageous if the channel and/or the sensor tape are/is provided with a coating reducing the friction. This coating may be solid, for example a Teflon® coating, manufactured by DuPont of Wilmington, Del., may be applied to the sensor tape. Another possibility is to use lubricants, such as glycerin or a sliding gel, on the precondition that the channel is designed to be leaktight.

Furthermore, the embodiments relate to a sensor tape for mounting in a flexurally limp carrier structure which allows a near-contour fastening on a surface, in particular that of a human or animal body. A sensor tape of this type is described in the prior art already indicated initially.

An aspect of the embodiments is to specify a sensor tape which allows mounting into a carrier structure to the effect that the composite sensor tape structure thus produced can be deformed, comparatively free of force.

This object is achieved according to the embodiments, by the specified sensor tape, in that the sensor tape has a reference point which can be connected to by the carrier structure as an essentially punctiform fixing device, the reference point being held non-displaceably on the carrier structure. Designing the sensor tape with a reference point achieves the advantages already described, to be precise that, on the one hand, the position of the sensor tape on the carrier structure is clearly defined at least at one point and, on the other hand, a longitudinal displaceability of the sensor tape on the carrier structure is possible when the carrier structure experiences an elastic change in length.

BRIEF DESCRIPTION OF THE DRAWINGS

These and other aspects and advantages will become more apparent and more readily appreciated from the following description of the exemplary embodiments, taken in conjunction with the accompanying drawings of which.

DETAILED DESCRIPTION OF THE PREFERRED EMBODIMENTS

Figure 1:
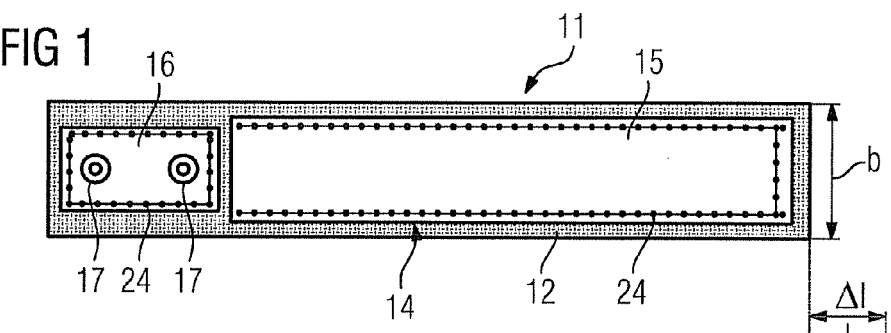
FIG. 1 shows an exemplary embodiment of the carrier structure embodiments as a top view.

A carrier structure 11 according to FIG. 1 includes a carrier tape 12 which forms the basis of the carrier structure. The carrier structure serves for receiving a sensor tape (strip) 13 (cf. FIG. 2) which can be pushed, for reliable mounting, into a pocket 14 which is formed by a textile strip 15 stitched to the carrier tape 12. The pocket 14 is closed on one side and is open on the other side, so that the sensor tape 13 can be pushed in from the open side. Furthermore, a relatively rigid patch 16 is stitched in front of the open side of the pocket 14 and carries two press stud fastenings 17 as a fixing device for the sensor tape 13. The rigidity of the patch ensures that this region having the press stud fastenings 17 does not copy the length changes Δl, indicated in FIG. 1, of the carrier tape, so that this region can be used as a reference point 18 of the sensor tape 13. To be fixed on the carrier tape 12, the sensor tape 13 has corresponding press stud fastenings, which cannot be seen in FIG. 2 since they face away from the picture face.

Figure 2:
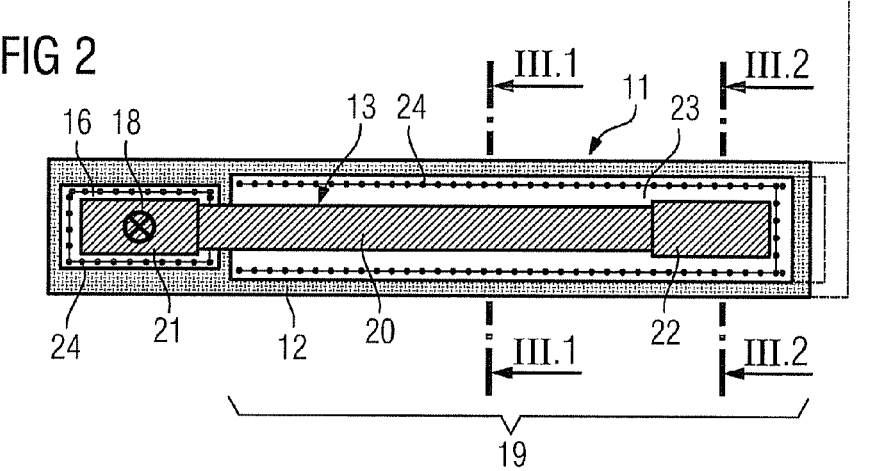
FIG. 2 shows a carrier structure, as shown in FIG. 1, without the textile strip illustrated in FIG. 1 and with an installed exemplary embodiment of the sensor tape.

FIG. 2 contains an illustration of the sensor tape 13 mounted on the carrier tape 12. The sensor tape includes the actual sensitive region 20, a transmission unit 21 and a reception unit 22. For the sake of simplicity, contacting is omitted or, for example, could be made wirelessly by a radio connection. The textile strip 15 is not illustrated in FIG. 2, even though it is present. It becomes clear that the carrier tape 12 has provided on it a coating 23 which improves the sliding properties and the extent of which corresponds to that of the textile strip 15. Furthermore, it can be gathered from FIGS. 1 and 2 that a connection of the individual components of the carrier structure 11 may take place, for example, by stitches 24. Another possibility is to weld or adhesively bond the components to one another. It should be noted that the connection technique must cover the length change of the carrier tape 12. Welding would be possible, for example, by individual welding spots. Adhesive joints would have to be adapted in terms of their elasticity values. The stitch used must be a stretchable stitch, for example, a zigzag stitch.

It can be gathered from FIG. 2, furthermore, that the sensor tape is illustrated in the shortened state, in which the shortened length of the pocket 14 is still just sufficient for receiving the sensor tape 13. The length of the carrier tape 12, including the pocket 14, in the relaxed state is illustrated by dashes and dots. What is indicated, furthermore, by dashes and dots is that the carrier tape can also be lengthened by half of $\Delta 1$.

Figure 3:
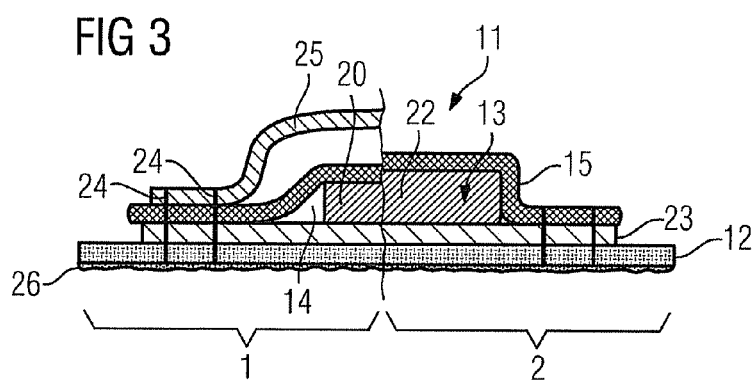
FIG. 3 shows the sections III.1 and III.2 according to FIG. 2.

In FIG. 3, the carrier structure 11 with the sensor tape 13 can be seen in cross section. Here, the sectional planes III.1 and III.2 according to FIG. 2 are illustrated and are identified by 1 and 2. It becomes clear that the flexible textile strip 15 can in each case be adapted to the contour of a sensor tape 13, thus ensuring that the latter is always pressed onto the base of the carrier tape 12 provided with the coating 23.

Furthermore, in the section III.1, a guard bridge 25 can be seen which is likewise firmly stitched to the carrier tape. The stitches 24 are likewise indicated. Lastly, it can be seen that the carrier tape 12 has an adhesive layer 26 on the underside which is to be fastened to the surface.

The following materials may be used for the carrier structure. The carrier tape 12 may be a tape sold under the trade name of CureTape®. This is elastic along its longitudinal extent ($\Delta 1$), but does not contract under elongation, instead preserving its width b. This tape is coated on the underside with a skin-compatible adhesive layer 26 and can thus be fastened firmly to the skin of a test person, for example at the back. The coating 23 may, for example, be a Teflon® coating which is spun onto the carrier tape 12. This coating is designed to be substantially thinner than illustrated in FIG. 3, so that it applies the necessary elasticity when the length of the carrier tape is changed by the amount $\Delta 1$. The textile strip 15 may be a highly elastic substance, such as has been developed, for example, from the production of bathing suits, for example Lycra® or Elaspan® manufactured by Invista of Wichita, Kans. The guards 25 may be a thermoplastic. This has, on the one hand, a sufficient safety against breakage and inherent stability to ensure that the sensor tape 20 is protected. On the other hand, it is sufficiently flexible so that it can follow the deformations of the carrier tape 12. If the carrier guard is provided with suitable holes, fastening by the stitch 24 can be achieved.

The sensor tape has a bend-sensitive configuration. Thus, the bends imparted to the carrier structure can be determined.

In this case, various operating principles may be implemented for the sensor tape. Preferably, as illustrated, the sensor tape 13 may be an optical sensor tape containing optical waveguides by which a measurement signal is transmitted. A different amount of light is output from the sensor fibers as a function of the bending of the latter, so that, by the transmitted light being determined in the receiver unit 22, it is possible to draw a conclusion as to the prevailing bending state of the sensor fiber and consequently of the carrier structure 11. The light is introduced via the transmission unit 21 into the sensitive unit 20 formed by the light guide fibers (not illustrated).

Of course, other measurement principles may also be envisaged, for example an electrical read-out of measurement signals is possible (capacitive or resistive elements).

A description has been provided with particular reference to preferred embodiments thereof and examples, but it will be understood that variations and modifications can be effected within the spirit and scope of the claims which may include the phrase "at least one of A, B and C" as an alternative expression that means one or more of A, B and C may be used, contrary to the holding in Superguide v. DIRECTV, 358 F3d 870, 69 USPQ2d 1865 (Fed. Cir. 2004).

The invention claimed is:

1. A flexurally limp carrier structure adapted to hold a sensor tape for near-contour fastening on a surface of a human or animal body, wherein the carrier structure comprises:
    a carrier tape which can be fastened by one side via adhesive to the surface and another side of the carrier tape which forms a wall part of a channel with the channel being provided for the sensor tape in which the sensor tape can be mounted so as to be longitudinally displaceable;
    an elastic textile strip which is firmly connected, at least along side margins of the elastic textile strip, to a part of the carrier structure to form a pocket with elastic in a direction of run of the channel, and
    a punctiform fixing device, by which the sensor tape can be held non-displaceably on the carrier structure at a reference point,
    wherein the carrier tape at least essentially preserves carrier tape width independently of carrier tape elongation.

2. The carrier structure as claimed in claim 1, wherein, in a non-deformed state of the carrier structure, the channel is longer a part of the sensor tape which is to be guided in the channel.

3. The carrier structure as claimed in claim 1, wherein the textile strip has a lower rigidity under extension than the carrier tape.

4. The carrier structure as claimed in claim 1, further comprising guard bridges which are spaced apart from one another to form the channel and which are fixed on the carrier structure in a longitudinal orientation with respect to the channel, and span a place of installation of the sensor tape.

5. The carrier tape as claimed in claim 1, wherein one of the channel and the sensor tape is provided with a coating reducing friction.

6. An apparatus, comprising:
    a sensor strip;
    an elastic support strip which on a first side forms one side of a pocket in which the sensor strip rests and having an adhesive on a second side for adhering the apparatus to a body; and
    a textile strip attached to the support strip to form a second side of the pocket and slidably holding the sensor strip,
    wherein the support strip at least essentially preserves support strip width independently of support strip elongation.

* * * * *

UNITED STATES PATENT AND TRADEMARK OFFICE
CERTIFICATE OF CORRECTION

PATENT NO.        : 8,435,191 B2                    Page 1 of 1
APPLICATION NO.   : 12/669321
DATED             : May 7, 2013
INVENTOR(S)       : Barboutis et al.

It is certified that error appears in the above-identified patent and that said Letters Patent is hereby corrected as shown below:

On the Title Page, Item (54) and in the Specification, In Column 1, Line 3, (Title), Delete "SAID" and insert -- THE --, therefor.

Signed and Sealed this
Twenty-fifth Day of March, 2014

Michelle K. Lee
*Deputy Director of the United States Patent and Trademark Office*